(12) United States Patent
Goltra

(10) Patent No.: US 9,864,838 B2
(45) Date of Patent: Jan. 9, 2018

(54) CLINICALLY INTELLIGENT PARSING

(75) Inventor: Peter S. Goltra, Middleburg, VA (US)

(73) Assignee: MEDICOMP SYSTEMS, INC., Chantilly, VA (US)

(*) Notice: Subject to any disclaimer, the term of this patent is extended or adjusted under 35 U.S.C. 154(b) by 595 days.

(21) Appl. No.: 12/071,375

(22) Filed: Feb. 20, 2008

(65) Prior Publication Data
US 2009/0210450 A1 Aug. 20, 2009

(51) Int. Cl.
G06F 17/30 (2006.01)
G06F 19/00 (2011.01)

(52) U.S. Cl.
CPC ........ *G06F 19/325* (2013.01); *G06F 19/3487* (2013.01); *G06F 19/327* (2013.01)

(58) Field of Classification Search
CPC ............. G06F 17/2705; G06F 17/2229; G06F 17/243; G06F 19/325; G06F 19/327; G06F 19/3487
USPC ........................................................ 704/1, 9
See application file for complete search history.

(56) References Cited

U.S. PATENT DOCUMENTS

| 5,794,208 A | | 8/1998 | Goltra | |
|---|---|---|---|---|
| 5,802,495 A | * | 9/1998 | Goltra | G06F 17/2229 704/1 |
| 5,809,476 A | * | 9/1998 | Ryan | G06Q 50/22 704/9 |
| 5,812,984 A | | 9/1998 | Goltra | |
| 5,823,948 A | | 10/1998 | Ross et al. | |
| 5,823,949 A | * | 10/1998 | Goltra | A61B 5/00 128/924 |
| 6,055,494 A | * | 4/2000 | Friedman | G06F 17/2705 704/9 |
| 6,182,029 B1 | * | 1/2001 | Friedman | G06F 17/2705 704/9 |
| 6,247,004 B1 | * | 6/2001 | Moukheibir | G06F 19/324 600/300 |
| 6,754,655 B1 | * | 6/2004 | Segal | G06F 17/278 |
| 6,915,254 B1 | * | 7/2005 | Heinze | G06F 17/27 382/225 |
| 6,955,647 B2 | * | 10/2005 | Rice | A61B 5/00 128/920 |
| 7,657,521 B2 | * | 2/2010 | Masarie | G06F 17/278 704/10 |
| 7,966,195 B2 | * | 6/2011 | Sanger | G06Q 10/00 705/2 |
| 2002/0035486 A1 | * | 3/2002 | Huyn | G06F 19/3418 705/3 |

(Continued)

OTHER PUBLICATIONS

Written Opinion mailed Aug. 3, 2009 in corresponding International Application No. PCT/US2008/013470.

(Continued)

*Primary Examiner* — Jean M Corrielus
(74) *Attorney, Agent, or Firm* — Buchanan Ingersoll & Rooney PC

(57) ABSTRACT

A method, a device and a system for correlating medical information of a first format to medical information of a second format are provided. The method includes parsing an input sequence representing textual information into plural terms; searching a medical database to associate each term with a medical diagnosis; and translating each term into a coded phrase previously associated with the medical diagnosis in the medical database.

33 Claims, 6 Drawing Sheets

(56) References Cited

U.S. PATENT DOCUMENTS

| | | | |
|---|---|---|---|
| 2003/0212576 A1* | 11/2003 | Kim | G06F 19/328 705/2 |
| 2003/0233031 A1* | 12/2003 | Rice | A61B 5/00 600/300 |
| 2003/0233251 A1 | 12/2003 | Haskell | |
| 2004/0078236 A1* | 4/2004 | Stoodley | G06F 19/322 705/2 |
| 2004/0243545 A1* | 12/2004 | Boone | G06F 19/322 |
| 2005/0010444 A1* | 1/2005 | Iliff | G06Q 50/22 705/2 |
| 2005/0192792 A1* | 9/2005 | Carus | G06F 17/2735 704/2 |
| 2005/0240439 A1* | 10/2005 | Covit | G06F 19/327 705/2 |
| 2006/0142645 A1* | 6/2006 | Rice | A61B 5/00 600/300 |
| 2007/0088695 A1* | 4/2007 | Bleyendaal | G06F 17/30696 |
| 2007/0198250 A1* | 8/2007 | Mardini | G06F 17/243 704/9 |
| 2008/0091464 A1* | 4/2008 | Lipscher | G06Q 50/22 705/2 |
| 2009/0018862 A1* | 1/2009 | Sanger | G06Q 10/00 705/2 |
| 2009/0119128 A1* | 5/2009 | Fitzgerald | G06F 19/3406 705/3 |
| 2014/0037162 A1* | 2/2014 | Papier | G06F 19/324 382/128 |
| 2016/0048651 A1* | 2/2016 | Papier | G06F 19/324 382/128 |
| 2017/0109487 A1* | 4/2017 | Fitzgerald | G06F 19/345 |

OTHER PUBLICATIONS

International Search Report mailed Aug. 3, 2009 in corresponding International Application No. PCT/US2008/013470.

* cited by examiner

CLINICALLY INTELLIGENT PARSING

FIELD OF THE DISCLOSURE

The present disclosure relates to a method, a device and a system for clinically intelligent parsing, which includes correlating medical information of a first format to medical information of a second format.

BACKGROUND

Medical practice generates a large amount of clinical data in natural language form, such as physicians' dictations, notes, records and test reports. The clinical data in natural language form lacks standardized structure, which can impact its effective use. The lack of standardized structure also affects interoperability of electronic medical records.

SUMMARY

The present disclosure provides a method, a device and a system for correlating medical information of a first format to medical information of a second format.

An exemplary method for correlating medical information of a first format to medical information of a second format is provided. The method includes parsing an input sequence representing textual information into plural terms; searching a medical database to associate each term with a medical diagnosis; and translating each term into a coded phrase previously associated with medical diagnosis in the medical database.

An exemplary device for correlating medical information of a first format to medical information of a second format is provided. The device includes a parsing means for parsing an input sequence representing textual information into plural terms; a searching means for searching a medical database to associate each term with a medical diagnosis; and a translating means for translating each term into a coded phrase previously associated with medical diagnosis in the medical database.

An exemplary system for correlating medical information of a first format to medical information of a second format is provided. The system includes a medical vocabulary file, and a medical database which includes coded phrases and coded diagnosis, and specifies relationships between the coded phrases and the coded diagnoses. The medical vocabulary file and the medical database can be accessed to parse the input sequence into plural terms. The medical database can be accessed to associate each term with a medical diagnosis; and translate each term into a coded phrase previously associated with medical diagnosis in the medical database.

An exemplary system for correlating medical information of a first format to medical information of a second format is provided. The system includes a processor, the processor being able to execute a software module; one or more data storage devices coupled to the processor, the data storage devices storing a medical vocabulary file, and a medical database; one or more input devices connected to the processor for sending an input to the processor; and a display device connected to the processor for displaying an output of the processor. The software module is executed to access the medical vocabulary file and the medical database to parse an input sequence representing textual information into plural terms, and to access the medical database to associate each term with a medical diagnosis, and translate each term into a coded phrase previously associated with the medical diagnosis in the medical database.

BRIEF DESCRIPTION OF THE DRAWINGS

These and other features of the present disclosure will be readily apparent to one of ordinary skill in the art from the following written description, used in conjunction with the drawings, in which.

DETAILED DESCRIPTION

Figure 1:
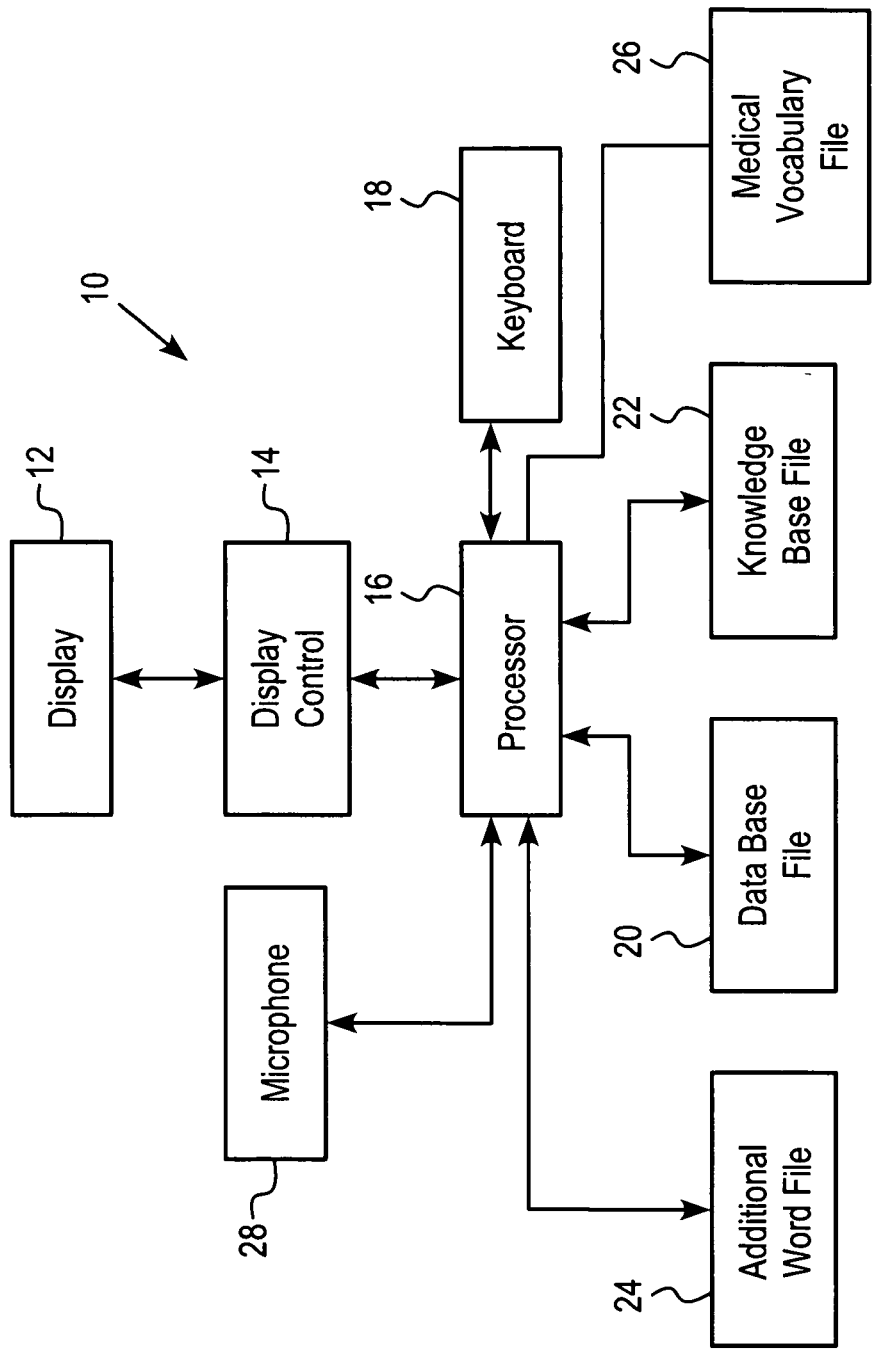
FIG. 1 illustrates a block diagram of a computer based medical system according to an embodiment of the present disclosure.

The present disclosure uses a computer based medical system, as illustrated in FIG. 1, to correlate medical information of a first format to medical information of a second format.

Referring to FIG. 1, a block diagram of the computer based medical system suitable for use in practicing the teachings of the present disclosure is illustrated. The medical system 10 contains a processor 16 with one or more input devices such as a keyboard 18. In addition, a microphone 28 can be used as an input device. The microphone 28 can have buttons which are programmable. A cursor on the screen can be controlled by input from the microphone 28. The processor 16 also has a database file or memory 20, a knowledge base file or memory 22, an additional word file or memory 24 and a medical vocabulary file or memory 26. The processor 16 operates a standard display controller 14 which in turn, controls a display device 12 at the work station. The display device 12 can be any standard type of display monitor, attached or wireless. Furthermore, the apparatus 10 can be networked to other such medical systems not illustrated which can be placed around a hospital or healthcare facility. This allows multiple people to use the medical system for the same or for multiple patients.

Medical findings are defined as symptoms, history, physical findings, diagnoses, tests, and therapy which may be present for a particular patient. The database file 20 can, for example, contain over 200,000 such medical findings and can be divided into categories such as symptoms, history, physical findings, diagnoses, tests, and therapy.

The exemplary descriptions of the medical findings stored in the database file 20 can be hierarchical and can have up to eight or more levels of description. The first level gives the simplest explanation of a medical finding, for example, a cough. The explanations become more detailed the lower the level. A first level finding may be a cough, while a second level finding may be a brassy cough. Another exemplary feature of the database file 20 is that all of the medical findings are uniquely named. For example, each medical finding can be assigned an internal number which uniquely identifies that particular medical finding.

In addition, each medical finding contains a code which indicates which category within the database file 20 the medical finding is associated with. For example, a medical finding may contain the code SYM to indicate that the medical finding is associated with the symptoms section; HIS to indicate that the medical finding is associated with the history section; PHY to indicate that the medical finding is associated with the physical section; DIS to indicate that the medical finding is associated with the diagnoses section; TST to indicate that the medical finding is associated with the test section; and RX to indicate that the medical finding is associated with the therapy section.

The medical system 10 can contain a knowledge base file 22. The knowledge base file 22 can, for example, contain a detailed description of over 2,000 diagnoses. The detailed description of the diagnoses uses the medical finding terms which can be stored in the database file 20. For each diagnosis, each medical finding associated with the diagnosis can be assigned a numerical value depending on how important such a medical finding may be to the diagnosis. For example, in the detailed description of the diagnosis for coronary artery stenosis, medical findings such as chest pain or discomfort and dyspnea (shortness of breath), which are strong showings of coronary artery stenosis, can be given high values while a lack of an appetite may not be described in the diagnoses at all or given a very low value. Thus, the values assigned to each medical finding within the detailed description can be proportional to how important such a medical finding is to the diagnosis.

The values can vary for a given medical finding depending on a plurality of factors such as age of the patient and timeframe, i.e., when a symptom occurred in relation to other symptoms. For example, a white blood cell count of 18,000 may be given a high value if the patient is an adult while the same medical finding is not given a value at all if the patient is a new-born child because this is normal for a new-born child.

The medical findings used in the detailed descriptions of the diagnoses can be all coded, with their respective internal numbers. In addition, over 400,000 links can be provided between the database file 20 and the knowledge base file 22. In other words, the findings in the database file 20 occur over 400,000 times in the knowledge base memory 22.

The detailed description of the diagnoses stored in the knowledge base file 22 contains lists of symptoms as well as personal and family history and physical findings which a patient should or may have experienced. In addition, the detailed diagnoses contain lists of tests, possible therapies, and medications which may be prescribed for the patient if the healthcare professional decides that the patient is experiencing a particular illness or problem.

As described above, the medical database, such as a database file or memory 20, a knowledge base file or memory 22, includes coded phrases and coded diagnosis, and specifies relationships between the coded phrases and the coded diagnoses.

Figure 4:
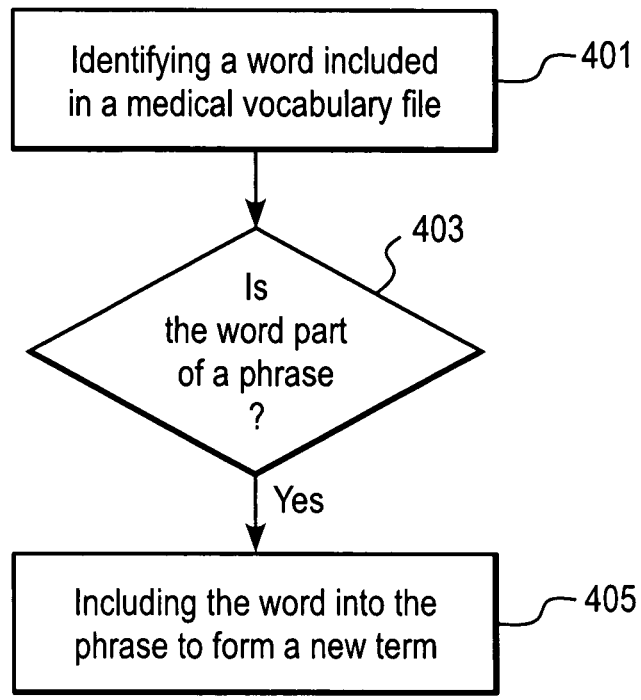
FIG. 4 illustrates an exemplary embodiment for parsing the input sequence.

The medical vocabulary file and the medical database can be accessed to parse the input sequence into plural terms, in a way that can be consistent with an exemplary embodiment illustrated in FIG. 4. The medical database can be accessed to associate each term with a medical diagnosis; and translate each term into a coded phrase previously associated with medical diagnosis in the medical database, in a way that can be consistent with an exemplary embodiment illustrated in FIGS. 5-7.

The additional word file 24 can be provided to list synonyms and alternate phrasings respectively corresponding to phrases. An exemplary embodiment of the additional word file 24 will be provided later.

Figure 2:
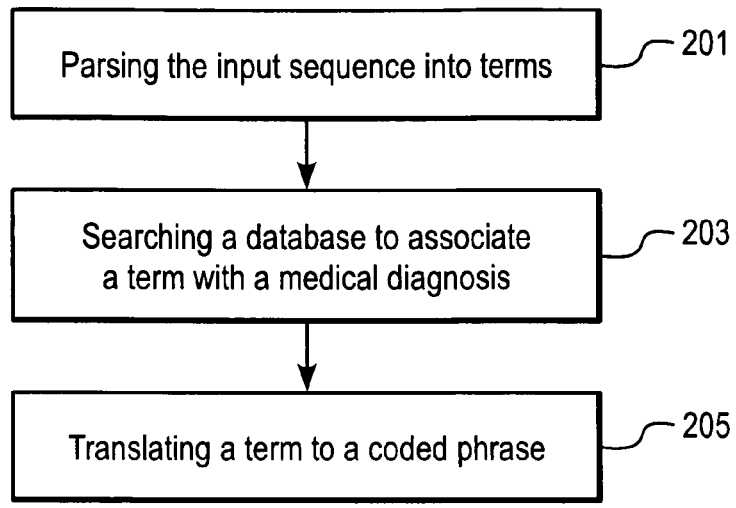
FIG. 2 illustrates a flow chart describing the operation of an embodiment of the present disclosure.
Figure 8:
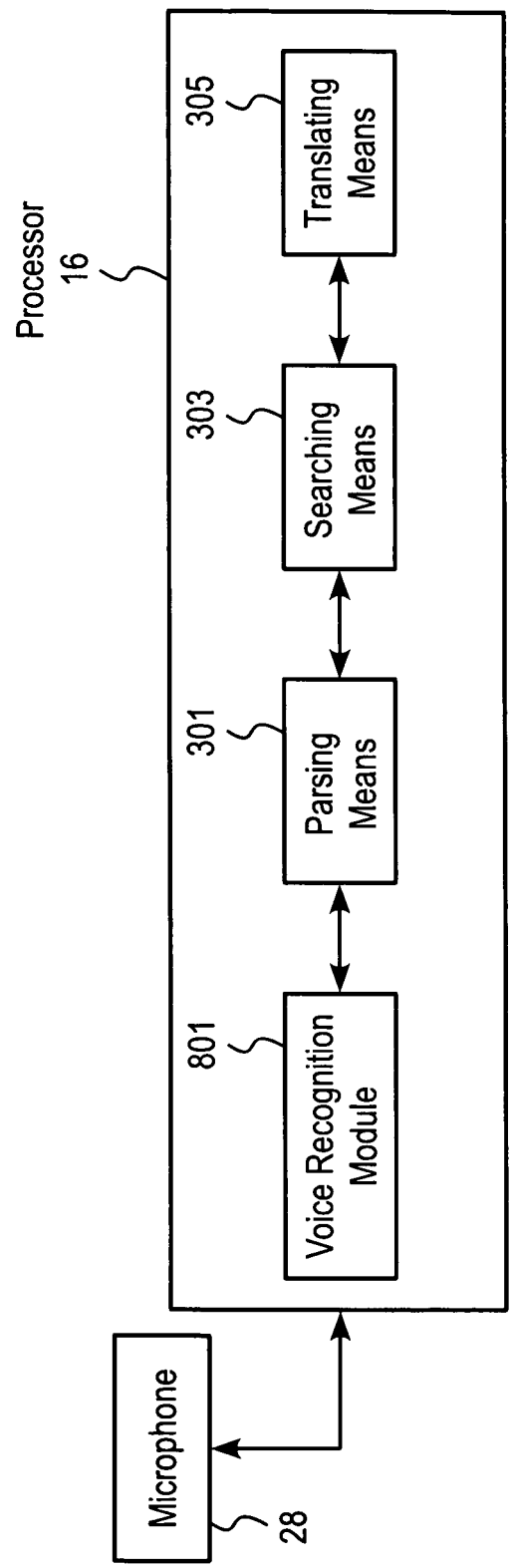
FIG. 8 illustrates an exemplary embodiment of an microphone, and a voice recognition module, a parsing means, a searching means and a translating means in a processor.

FIG. 2 describes the operation of an embodiment of the present disclosure. Referring to FIG. 2, in block 201, a process flow parses an input sequence representing textual information into plural terms. The input sequence can be a transcribed voice input, a recording of a physician's dictation, or a live dictation. For example, the input sequence can be a transcribed live dictation received from the microphone 28. FIG. 8 illustrates an exemplary embodiment of an microphone, and a voice recognition module, a parsing means, a searching means and a translating means in a processor. In FIG. 8, a voice recognition software module 801 receives input from the microphone 28. The voice recognition software module 801 is executable to transcribe the input from the microphone 28 into textual information. The output from the voice recognition module 801 can be the input sequence representing textual information to the parsing means 301. The voice recognition software module 801 can be various systems, e.g., Philip's SPEECHMAGIC, Dragon Systems' NATURALLY SPEAKING, and systems by IBM, or by Microsoft. A term can contain one or more words. In block 203, the process flow searches a medical database to associate each term with a medical diagnosis. In block 205, the process flow translates each term into a coded phrase previously associated with medical diagnosis in the medical database. A phrase can contain one or more words. A computer readable medium can store a program, which when executed causes a processor to perform the operation illustrated in FIG. 2.

Figure 3:
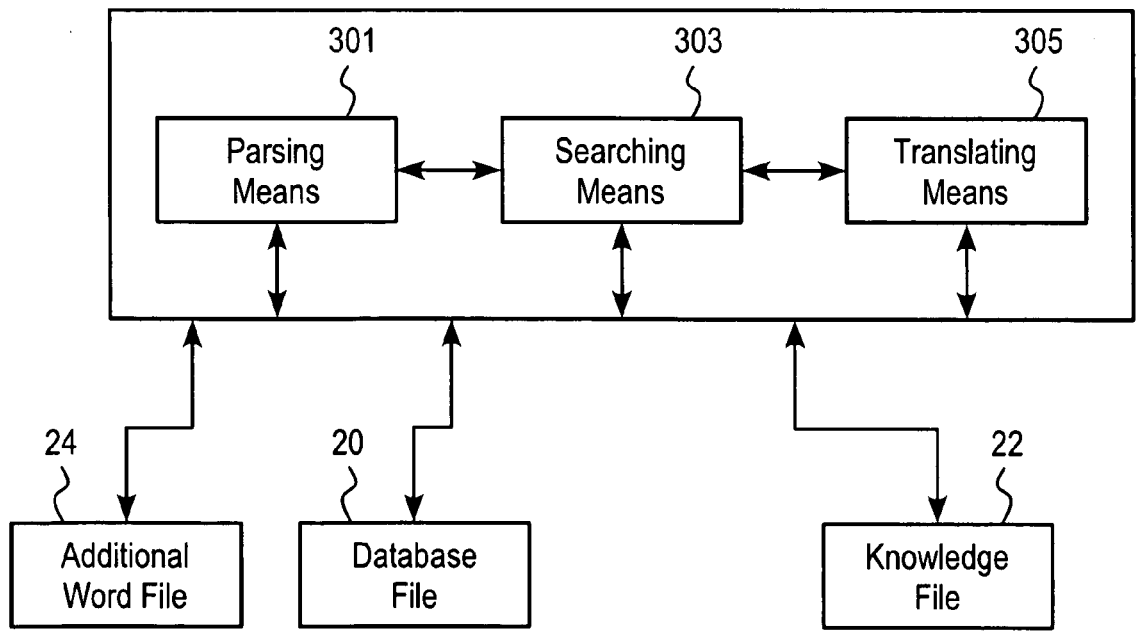
FIG. 3 illustrates a device according to an embodiment of the present disclosure.

FIG. 3 illustrates a device according to an embodiment of the present disclosure. Referring to FIG. 3, a parsing means 301 can parse the input sequence representing textual information into plural terms, according to the exemplary embodiment described in block 201. A searching means can search a medical database, for example, a database file or memory 20, a knowledge base file or memory 22, or an additional word file or memory 24, to associate each term with a medical diagnosis, according to the exemplary embodiment described in block 203. A translating means can translate each term into a coded phrase previously associated with medical diagnosis in the medical database, according to the exemplary embodiment described in block 205.

The various means described above can be implemented in conjunction with a computer-based system, including hardware, software, firmware, or combinations thereof.

For example, the various means can be implemented in separate software modules. The software modules can be executable in a shared processor. Alternatively, the software modules can be executable in dedicated processors, each of the processors dedicated to one of the software modules.

The various means can also be implemented in one software module, as illustrated in FIG. 3.

FIG. 4 illustrates an exemplary embodiment for parsing the input sequence. In block 401, a process flow identifies a word of input sequence included in a medical vocabulary file. The medical vocabulary file can be the MEDCIN Vocabulary file. In decision block 403, it is determined whether the word is part of a phrase of the input sequence using the medical database. If it is determined that the word is part of the phrase, including the word into the phrase to form a new term, as shown in block 405.

An illustrative pseudocode representation of such exemplary embodiment for parsing the input sequence is as follows:

```
VARIABLES
Array term[j]
Arrray Input_Sequence[i];
Integer Int_Length;
Boolean Flag_word;
Boolean Flag_term;
  BEGIN
  Input_Sequence [i] = words in the input sequence that represents the
textual information;
  Int_Length = number of words in the input sequence;
  i=1;
  j=1;
  While i<=Int_Length (the 1st while loop)
  Do
      Flag_word = Is Input_Sequence[i] a word included in a medical
      vocabulary file?
      i++;
  Until Flag_word = yes
  term [j] = Input_Sequence [i-1]
  Flag_term = are term[j] and Input_Sequence[i] part of a phrase?
  While Flag_term = yes (the 2nd while loop)
      term[j] = term[j] + Input_Sequence[i];
      i++;
      Flag_term = are term[j] and Input_Sequence[i] part of a phrase?
  End of the 2nd while loop;
  j++;
  End of the 1st while loop.
END
```

As mentioned above, a parsing means can be a software module which contains code that corresponds to the pseudocode above. The software module can be stored in any suitable memory, and executed by a dedicated processor of the parsing means, or by a common processor that is shared by the parsing means, the searching means and the translating means.

The words in an input sequence are processed sequentially and parsed into plural terms. Before such sequential processing, the input sequence can be pre-processed by deleting words that are included in an ignore word file from the input sequence. The ignore word file can include words that have limited relationship to any medical phrases, for example, prepositions.

To accommodate differences in expression in natural language, an additional word file 24 can be provided to list synonyms and alternate terms corresponding to terms. Alternative terms associated with a phrase can be determined by searching the additional word file 24. Determining the alternative terms can include selecting one or more of the alternative terms that have the strongest correlation with terms that immediately precedes and succeeds the term. Degree of correlation between two terms can be determined by the size of intersection set between diagnoses which refer to the two terms in a medical database, such as the database file 20, or the knowledge base file 22.

Figure 5:
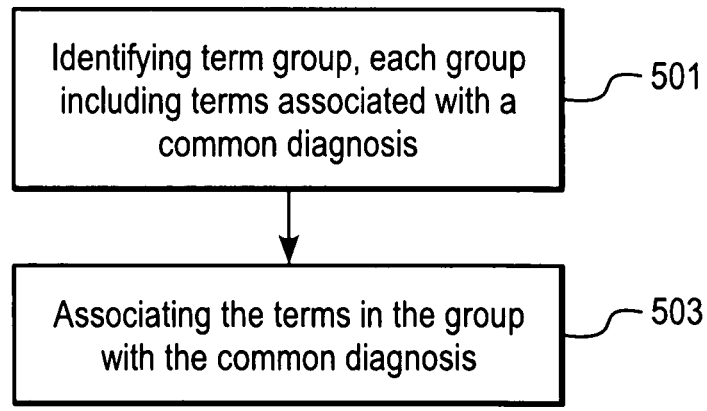
FIG. 5 illustrates an exemplary embodiment for searching the database to associate each term with a medical diagnosis.

FIG. 5 illustrates an exemplary embodiment for searching the database to associate each term with a medical diagnosis. Referring to FIG. 5, in block 501, a process flow identifies term groups among the terms, each term group including terms associated with at least one common diagnosis. In block 502, the process flow associates each term in the term group with the at least one common diagnosis.

Figure 6:
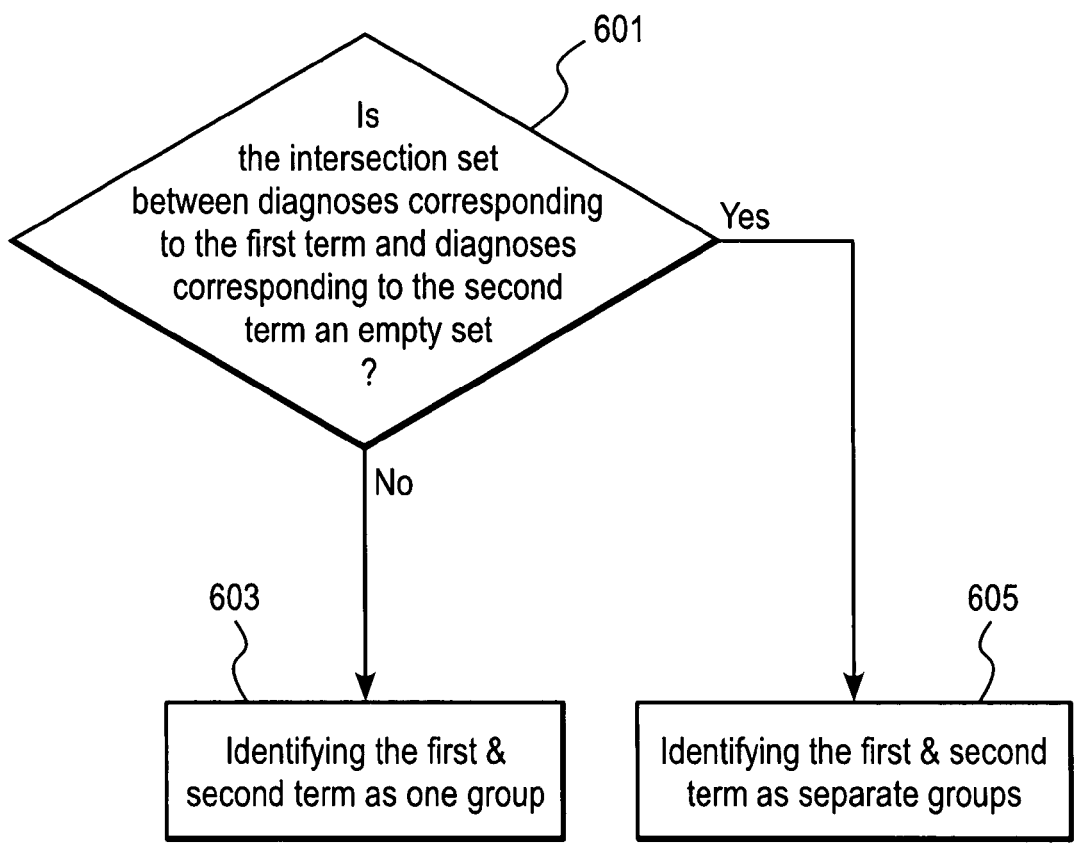
FIGS. 6 and 7 further illustrate the exemplary embodiment for searching the database to associate each term with a medical diagnosis

FIG. 6 further illustrates an exemplary embodiment for searching the database to associate each term with a medical diagnosis. Referring to FIG. 6, in decision block 601, it is determined whether an intersection set between one or more diagnoses corresponding to the first of plural terms and one or more diagnoses corresponding to the second of the plural terms, which is a first intersection set, is a non-empty set. The diagnoses corresponding to a term includes the diagnoses which refer to the term in a medical database. As mentioned above, values can be assigned to a coded phrase that are proportional to how important such a phrase is to the diagnosis. A diagnosis corresponds to a coded phrase when the value assigned to the coded phrase for that diagnosis is significant, for example, when the value exceeds a threshold. If the first intersection set is a non-empty set, the process flow identifies the first term and the second term as part of one group, as shown in block 603. If the first intersection set is an empty set, determine the first phrase as a first group, the process flow identifies the first term and the second term as being in separate groups.

Figure 7:
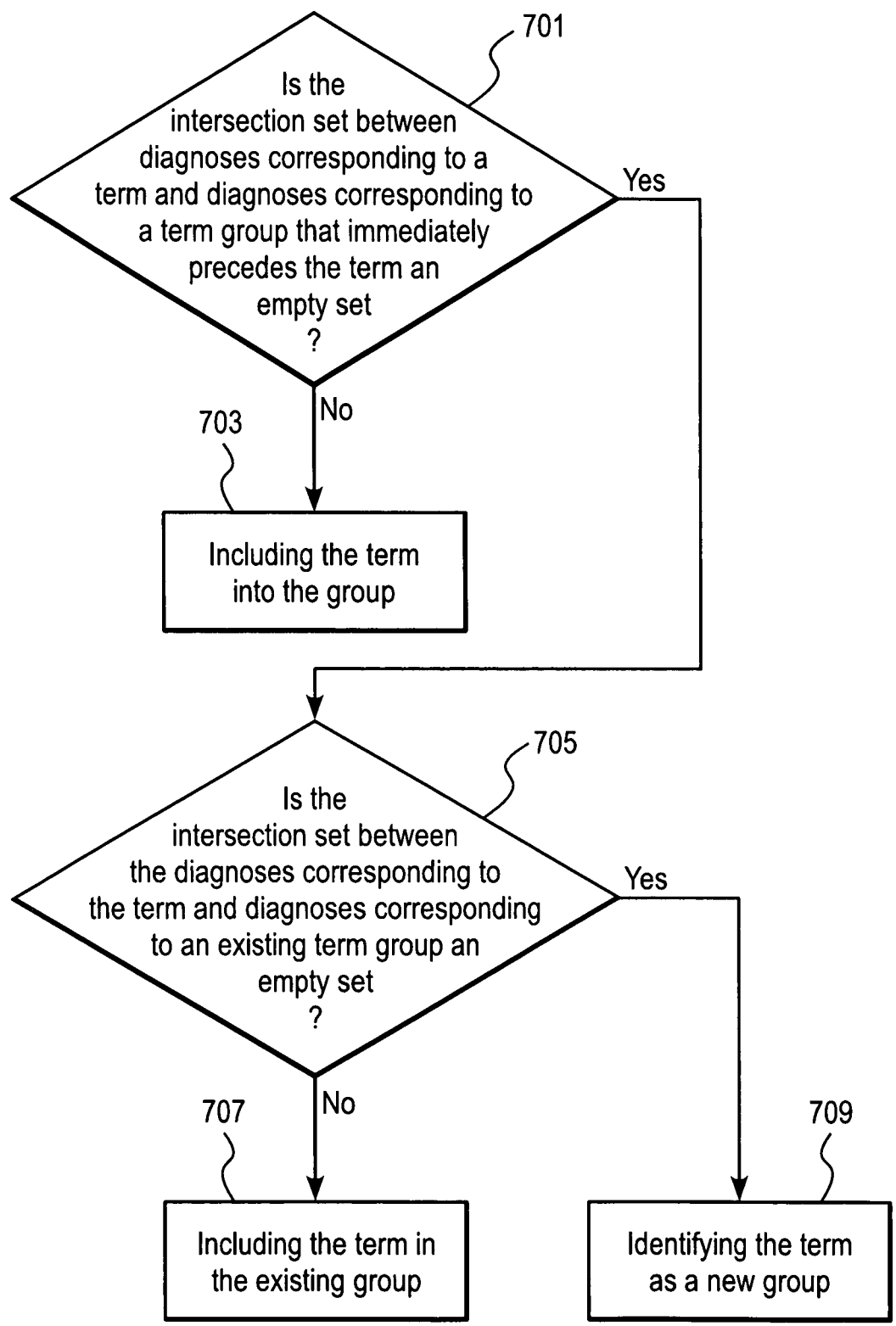

FIG. 7 further illustrates an exemplary embodiment for searching the database to associate each term with a medical diagnosis. Referring to FIG. 7, in decision block 701, it is determined whether an intersection set between one or more diagnoses corresponding to the term and one or more diagnoses corresponding to a term group that immediately precedes the term, which is a second intersection set, is a non-empty set. If the second intersection set is a non-empty set, the process flow includes the term into the immediately preceding term group, as shown in block 703. If the second intersection set is an empty set, it is determined whether an intersection set between the one or more diagnoses corresponding to the term and one or more diagnoses corresponding to an existing term group, which is a third intersection set, is a non-empty set, shown in decision block 705. If the third intersection set is a non-empty set, the process flow includes the term into the existing term group, shown in block 707. If the third intersection set is an empty set, the process flow identifies the term as part of a new term group, shown in block 709. According to the exemplary embodiment for combining phrases into groups, each group of phrases is more likely to be related to a diagnosis or related diagnoses.

The grouping of the phrases can be affected by the instructions included in the input sequence. For example, the input sequence can include an instruction indicating that content following the instruction relates to a diagnosis. Once such instruction is detected, the one or more terms in a term group immediately successive to the first instruction can be translated into coded phrases associated with the diagnosis indicated in the first instruction in the medical database.

As another example, the input sequence can include an instruction indicating that content following the instruction further describes a medical problem previously described in the input sequence. Once the second instruction is detected, an existing term group related to the medical problem indicated in the instruction can be identified; and the group immediately successive to the instruction can be combined into the identified existing group. For example, a physician's dictation used as the input sequence may contain the following parts in a sequence: the first part, descriptions of a patient's problem related to coronary artery; the second part, descriptions of another problem related to lack of an appetite; and the third part, descriptions back to the problem related to coronary artery. If an instruction is included before the third part of the dictation, indicating that the content following the instruction further describes the problem related to coronary artery as described in a prior part of the dictation, the existing term group relating to such prior part can be identified, and the term group of phrases following the instruction can be combined into the identified existing group.

It is noted that parsing of the input sequence into terms and identifying term groups can be performed concurrently. For example, the parsing the input sequence and the identifying the term groups can be performed concurrently with nested loop. An outer loop of the nested loop can execute the parsing the input sequence, and an inner loop can execute the identifying the term groups.

An illustrative pseudocode representation of an exemplary embodiment for parsing of the input sequence and identifying the term groups is as follows:

```
VARIABLES
Array Phrase[j]
Arrray Input_Sequence[i];
Array Group[m];
Integer Int_Length;
Integer counter;
Boolean Continue;
Boolean Flag_word;
Boolean Flag_term;
Boolean Flag_group;
BEGIN
Input_Sequence [i] = words in the input sequence that represents the
textual information;
Int_Length = number of words in the input sequence;
i=1;
j=1;
m=1;
counter=1;
While i<=Int_Length (the 1st while loop)
    Do
        Flag_word = Is Input_Sequence[i] a word included in a medical
vocabulary file?
        i++;
    Until Flag_word = yes
    term [j] = Input_Sequence [i-1]
    Flag_term = are term [j] and Input_Sequence[i] part of a phrase?
    While Flag_term = yes (the 2nd while loop)
        term[j] = term[j] + Input_Sequence[i];
        i++;
        Flag_term = are term[j] and Input_Sequence[i] part of one or
more coded phrases?
    End of 2nd while loop;
    Continue = yes
    While Continue =yes, do (the 3rd while loop);
        If j=1, then (the 1st if clause)
            group[1] = term[1];
        Else (else clause of the 1st if clause)
            Flag_group = Is the intersection set between one or more
diagnoses corresponding to term[j] and one or more diagnoses
corresponding to group[counter] a non-empty set?
            If Flag_group = yes, then (the 2st if clause)
                group[counter] = group[counter] + term[j];
                Continue = no;
            Else (else clause of the 2nd if clause)
                counter ++;
                If counter >m, then (the 3rd if clause)
                    Continue = no;
                    m++;
                    group[m] = phrase[j]
                Else (else clause of the 3rd if clause)
                    Continue = yes;
                End if; (end of the 3rd if clause)
            End if; (end of the 2nd if clause)
        End if; (end of the 1st if clause)
    End of the 3rd while loop;
    j++;
End of 1st while loop.
END
```

As mentioned above, a parsing means and a searching means can be a software module or modules which contain code that corresponds to the pseudocode above. The software module can be stored in any suitable memory, and executed by a dedicated processor for each of the parsing means, searching means and translating means, or by a common processor that is shared by the parsing means, the searching means and the translating means.

According to the exemplary embodiments, clinical data in a narrative natural language form can be converted into a structured form. Such natural language processing can facilitate maintaining electronic medical records, and enhancing interoperability of electronic medical records, among other things.

Once the input sequence is translated into coded phrases, such coded phrases can be output to be used to select from a plurality of clinical protocol forms. The clinical protocols are a structured combination of coded medical phrases selected from a structured medical database of coded phrases and are presented in the order of appearance selected by the healthcare professional. The protocols have a wide variety of uses. They can be used for routine examinations. They can also be used for a specific problem, such as the flu or angina. They can also be used for specific situations where a specified set of questions must always be asked or where certain information needs to be passed along to the patient. Since the number of possible clinical protocol forms could be large, it can be time-consuming for a healthcare professional to select a clinical protocol form that is related to a specific medical problem. According to an exemplary embodiment, the coded phrased translated from the input sequence can be output to be used to select a clinical protocol form that is related to a specific medical problem, for example, by calculating a matching rate of the translated coded phrases with the coded phrases contained in each of the clinical protocol form, and selecting the form with the highest matching rate.

In addition, the coded phrases translated from the input sequence can be output as an input of a system which receives coded phrases as input. For example, the translated coded phrases can be used as the input of an intelligent prompting system. In an intelligent prompting system, a healthcare professional can input medical finding for a patient into the system. The possible diagnoses are then ranked in descending point total. Once the highest ranked diagnoses have been selected, the healthcare professional can be prompted with additional findings associated with the selected diagnoses which have not yet been inputted into the clinical protocol. Intelligent prompting is more fully disclosed in U.S. Pat. No. 5,823,949, entitled "Intelligent Prompting," the entire contents of which are expressly incorporated herein by reference in their entirety. The translated coded phrases can be used an input of the intelligent prompting system, instead of having a healthcare professional inputting medical finding in the system.

It will be appreciated by those of ordinary skill in the art that the present disclosure can be embodied in other specific forms without departing from the spirit or essential character thereof. The presently disclosed embodiments are therefore considered in all respects to be illustrative and not restrictive. The scope of the disclosure as indicated by the appended claims rather than the foregoing description, and all changes which come within the meaning and range of equivalents thereof are intended to be embraced therein.

What is claimed is:

1. A device of correlating medical information of a first format to medical information of a second format, the device comprising:
   a parsing means for parsing an input sequence representing textual information into plural terms;
   a searching means for searching a medical database to associate each term with a medical diagnosis and an additional word memory for synonyms of each parsed term and selecting at least one synonym term having a degree of correlation with a respective medical diagnosis in the medical database that is above a predetermined threshold;

a translating means for translating each searched and selected term into a coded phrase wherein each coded phrase classifies a respective term in one of plural categories of medical findings associated with the medical diagnosis and stored in the medical database;

computing means for determining a point total for each medical diagnosis based on a total number of coded phrases associated with each medical diagnosis, and ranking the medical diagnoses based on respective point totals; and output means for outputting at least one of the input sequence, the parsed terms, and the coded phrase to a display and prompting a user with additional medical findings which have not yet been entered into the medical database upon selection of a highest medical ranked diagnosis.

2. The device of claim 1, wherein the parsing means, the searching means and the translating means are implemented in separate software modules.

3. The device of claim 2, wherein the software modules are executable in a shared processor.

4. The device of claim 2, wherein each of the software modules is executable in a dedicated processor, each dedicated processor being dedicated to one of the software modules.

5. The device of claim 1, wherein the parsing means, the searching means and the translating means are implemented in a shared software module.

6. The device of claim 1, wherein the coded phrase is selected from the categories of medical findings in the medical database consisting of: medical symptom, medical history, physical, medical test, and therapy.

7. A system correlating medical information of a first format to medical information of a second format, the system comprising:

a processor, the processor being able to execute a software module;

one or more data storage devices coupled to the processor, the data storage devices storing a medical vocabulary file, and a medical database;

one or more input devices connected to the processor for sending input to the processor; and a display device connected to the processor for displaying an output of the processor;

wherein the software module is executed to: access the medical vocabulary file and the medical database to parse an input sequence representing textual information into plural terms, access the medical database and perform a search to associate each parsed term with a medical diagnosis, which includes access an additional word memory for synonyms of each parsed term and selecting at least one synonym term having a degree of correlation with a respective medical diagnosis in the medical database that is above a predetermined threshold, translate each searched and selected term into a coded phrase, determine a point total for each medical diagnosis based on a total number of coded phrases associated with each medical diagnosis, rank the medical diagnoses based on respective point totals, provide each searched and selected term and the coded phrase to the output of the processor, and prompt a user with additional medical findings which have not yet been entered into the medical database upon selection of a highest medical ranked diagnosis, wherein each coded phrase classifies a respective term in one of plural categories of medical findings associated with the medical diagnosis and stored in the medical database.

8. The system of claim 7, wherein the one or more input devices comprise a microphone.

9. The system of claim 8, wherein a cursor of the display device is controlled by an input to the microphone.

10. The system of claim 8, wherein the system further comprises a voice recognition software module which is executable to transcribe input to the microphone into textual information.

11. The system of claim 7, wherein the coded phrase is selected from the categories of medical findings in the medical database consisting of: medical symptom, medical history, physical, medical test, and therapy.

12. A method of correlating medical information of a first format to medical information of a second format in a system having an input device, at least one processor, a first memory, and a second memory, the method comprising:

receiving, in the input device, an input sequence representing textual information; and in at least one first processor:

parsing the input sequence into plural terms;

searching a medical database to associate each term with a medical diagnosis, which includes searching an additional word memory for synonyms of each parsed term and selecting at least one synonym term having a degree of correlation with a respective term in the medical database that is above a predetermined threshold, wherein the searching the medical database includes: identifying term groups, each term group including terms associated with at least one common diagnosis; and associating each term in the term group with the at least one common diagnosis, wherein the term groups are identified by: determining whether an a first intersection set between one or more diagnoses corresponding to the first of plural terms and one or more diagnoses corresponding to the second of the plural terms is an empty set; if the first intersection set is a non-empty set, identifying the first term and the second term as part of one group; and if the first intersection set is an empty set, identifying the first term and the second term as being in separate groups;

translating each searched and selected term into a coded phrase wherein each coded phrase classifies a respective term into one of plural categories of medical findings associated with the medical diagnosis and stored in the medical database;

outputting at least one of the input sequence, the parsed terms, and the coded phrase to at least one of a second processor and a display; and in the at least one second processor:

determining a point total for each medical diagnosis based on a total number of coded phrases associated with each medical diagnosis;

ranking the medical diagnoses based on respective point totals; and prompting a user with additional medical findings not yet entered upon selection of a highest medical ranked diagnosis.

13. The method of claim 12, wherein the parsing of the input sequence comprises:

sequentially processing the input sequence by:

identifying whether a word of input sequence is included in a medical vocabulary file;

determining whether the word is part of a phrase of the input sequence using the medical database; and if the word is part of the phrase, including the word into the phrase to form a new term.

14. The method of claim 12, wherein the term groups are identified by:
sequentially processing each remaining term in the parsed input sequence by:
determining whether an intersection set between one or more diagnoses corresponding to the term and one or more diagnoses corresponding to a term group that immediately precedes the term, which is a second intersection set, is an empty set;
if the second intersection set is a non-empty set, including the term into the immediately preceding term group.

15. The method of claim 14, wherein:
if the second intersection set is an empty set, determining whether an intersection set between the one or more diagnoses corresponding to the term and one or more diagnoses corresponding to an existing term group, which is a third intersection set, is an empty set; and
if the third intersection set is a non-empty set, including the term into the existing term group; and
if the third intersection set is an empty set, identifying the term as part of a new term group.

16. The method of claim 12, wherein the parsing of the input sequence and the identifying of the term groups are performed concurrently.

17. The method of claim 12, wherein the parsing of the input sequence and the identifying of the term groups are performed concurrently with a nested loop, an outer loop of the nested loop executing the parsing of the input sequence, and an inner loop executing the identifying of the term groups.

18. The method of claim 12, comprising:
deleting any word that is included in an ignore word file from the input sequence before the parsing the input sequence.

19. The method of claim 18, wherein the ignore word file includes prepositions.

20. The method of claim 12, comprising:
determining alternative terms associated with a term by searching an additional word file.

21. The method of claim 20, wherein determining the alternative terms comprises:
selecting one or more of the alternative terms that have the strongest correlation with terms that immediately precede and succeed the term.

22. The method of claim 21, wherein a degree of correlation between two terms is determined by the size of intersection set between diagnoses which refer to the two terms in the medical database.

23. The method of claim 12, wherein the input sequence comprises:
a voice input that has been transcribed.

24. The method of claim 12, wherein the input sequence comprises:
a recording of a dictation.

25. The method of claim 12, wherein the input sequence comprises:
a live dictation.

26. The method of claim 12, wherein the input sequence representing textual information comprises:
one or more instructions.

27. The method of claim 26, wherein the one or more instructions comprise:
a first instruction indicating that content following the first instruction relates to a diagnosis.

28. The method of claim 27, comprising:
detecting the first instruction; and
translating the one or more terms in a term group immediately successive to the first instruction into coded phrases associated with the diagnosis indicated in the first instruction in the medical database.

29. The method of claim 26, wherein the one or more instructions comprise:
a second instruction indicating that content following the second instruction describes a medical problem previously described in the input sequence.

30. The method of claim 29, comprising:
detecting the second instruction;
identifying an existing term group relating to the medical problem indicated in the second instruction; and
identifying terms in a term group immediately successive to the second instruction and the identified existing term group as one group.

31. The method of claim 12, comprising:
outputting the translated phrases; and
selecting from a plurality of clinical protocol forms based on the output.

32. The method of claim 12, wherein the method comprises:
outputting the translated phrases; and
using the output as an input of a system which receives coded phrases as input.

33. A non-transitory computer readable medium having stored therein a program, which when executed causes a processor to perform a method of correlating medical information of a first format to medical information of a second format in a system having an input device, at least one processor, a first memory, and a second memory, the method comprising:
receiving, in the input device, an input sequence representing textual information; and
in at least one first processor:
parsing the input sequence into plural terms;
searching a medical database to associate each term with a medical diagnosis, which includes searching an additional word memory for synonyms of each parsed term and selecting at least one synonym term having a degree of correlation with a respective term in the medical database that is above a predetermined threshold, wherein the searching the medical database includes: identifying term groups, each term group including terms associated with at least one common diagnosis; and associating each term in the term group with the at least one common diagnosis, wherein the term groups are identified by: determining whether an a first intersection set between one or more diagnoses corresponding to the first of plural terms and one or more diagnoses corresponding to the second of the plural terms is an empty set; if the first intersection set is a non-empty set, identifying the first term and the second term as part of one group; and if the first intersection set is an empty set, identifying the first term and the second term as being in separate groups;
translating each searched and selected term into a coded phrase wherein each coded phrase classifies a respective term into one of plural categories of medical findings associated with the medical diagnosis and stored in the medical database;
outputting at least one of the input sequence, the parsed terms, and the coded phrase to at least one of a second processor and a display; and in the at least one second processor:

determining a point total for each medical diagnosis based on a total number of coded phrases associated with each medical diagnosis;

ranking the medical diagnoses based on respective point totals; and prompting a user with additional medical findings not vet entered upon selection of a highest medical ranked diagnosis.

* * * * *